United States Patent

Natsume et al.

[11] Patent Number: 5,185,354
[45] Date of Patent: Feb. 9, 1993

[54] PYRAZOLECARBOXAMIDE, INSECTICIDAL AND MITICIDAL COMPOSITION, AND FUNGICIDAL COMPOSITION FOR USE IN AGRICULTURE AND HORTICULTURE

[75] Inventors: Bunji Natsume, Yokohama; Nobuo Kyomura, Sagamihara; Kazuhiko Kikutake, Yokohama; Toshiki Fukuchi, Machida, all of Japan

[73] Assignee: Mitsubishi Kasei Corporation, Tokyo, Japan

[21] Appl. No.: 716,109

[22] Filed: Jun. 17, 1991

[30] Foreign Application Priority Data

Jun. 18, 1990 [JP] Japan .................. 2-158991

[51] Int. Cl.$^5$ .................. C07D 417/12; A01N 43/78
[52] U.S. Cl. .................. 514/369; 514/365; 548/181; 548/187; 548/204
[58] Field of Search .................. 548/204, 181, 187; 514/365, 369

[56] References Cited

U.S. PATENT DOCUMENTS

| | | | |
|---|---|---|---|
| 4,950,668 | 8/1990 | Okada | 548/378 |
| 5,039,694 | 8/1991 | Suzuki | 548/374 |

FOREIGN PATENT DOCUMENTS

| | | |
|---|---|---|
| 0268892 | 6/1988 | European Pat. Off. |
| 0289879 | 11/1988 | European Pat. Off. |
| 0329020 | 8/1989 | European Pat. Off. |

Primary Examiner—Robert Gerstl
Attorney, Agent, or Firm—Oblon, Spivak, McClelland, Maier & Neustadt

[57] ABSTRACT

A pyrazolecarboxamide derivative represented by the following formula (I):

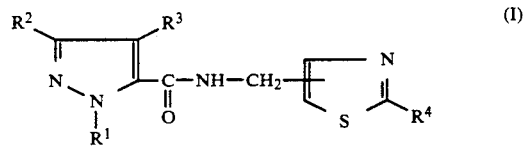

wherein $R^1$ represents a $C_1\sim C_3$ alkyl group, $R^2$ represents a $C_1\sim C_3$ alkyl group, $R^3$ represents a hydrogen atom or halogen atom, $R^2$ and $R^3$ may combine to form a $C_3\sim C_4$ alkylene group which may be substituted by a $C_1\sim C_3$ alkyl group, and $R^4$ represents a $C_1\sim C_6$ alkyl group, benzyl group which may be substituted or a group represented by $-XR^5$ wherein X represents an oxygen atom, sulfur atom, sulfinyl group or sulfonyl group and $R^5$ represents a $C_1\sim C_8$ alkyl group, $C_2\sim C_6$ alkenyl group, $C_3\sim C_7$ cycloalkyl group which may be substituted by a $C_1\sim C_3$ alkyl group, $C_1\sim C_5$ haloalkyl group or phenyl group which may be substituted, an insecticidal and miticidal composition containing the pyrazolecarboxamide derivative as the active ingredient, and a fungicidal composition for use in agriculture and horticulture containing the pyrazolecarboxamide derivative as the active ingredient are provided.

9 Claims, No Drawings

PYRAZOLECARBOXAMIDE, INSECTICIDAL AND MITICIDAL COMPOSITION, AND FUNGICIDAL COMPOSITION FOR USE IN AGRICULTURE AND HORTICULTURE

BACKGROUND OF THE INVENTION

The present invention relates to a pyrazolecarboxamide derivative. The present invention further relates to an insecticidal and miticidal composition and a fungicidal composition, which contain the pyrazolecarboxamide derivative as the active ingredient.

Recently, harmful insects and mites have acquired resistance to chemicals such as insecticides and miticides because such chemicals have been used long time, and as a result of it, the control of such chemical resistant insects and mites by the conventional insecticides and miticides has become difficult. For example various kinds of harmful insects and mites have acquired resistance to typical insecticides such as organic phosphorus agents and carbamates and control thereof has become a problem to be solved. Further, the acquirement of resistance to synthetic pyrethroides has been also reported. In addition, some pathogenic fungi have also acquired resistance to the conventional fungicides. As a result thereof, the control of disease damage by the conventional fungicides has become low in controlling effect, and the control of such resistant fungi become serious problem to be solved. Accordingly, it has been expected to develop a novel insecticide, miticide and fungicide for use in agriculture and horticulture having activity for controlling such resistant insects, mites and fungi.

The present inventors have made an earnest study for solving the above problem and have found a pyrazolecarboxamide derivative having excellent insecticidal activity, miticidal activity and fungicidal activity. The present invention has been accomplished based on this finding.

SUMMARY OF THE INVENTION

The present invention provide a pyrazolecarboxamide derivative represented by the following formula (I):

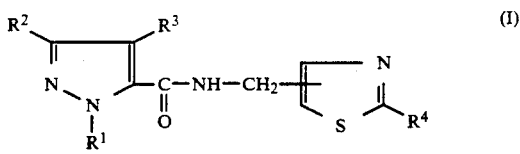

wherein $R^1$ represents a $C_1 \sim C_3$ alkyl group, $R^2$ represents a $C_1 \sim C_3$ alkyl group, $R^3$ represents a hydrogen atom or halogen atom, $R^2$ and $R^3$ may combine to form a $C_3 \sim C_4$ alkylene group which may be substituted by a $C_1 \sim C_3$ alkyl group, and $R^4$ represents a $C_1 \sim C_6$ alkyl group, benzyl group which may be substituted or a group represented by $-XR^5$ wherein X represents an oxygen atom, sulfur atom, sulfinyl group or sulfonyl group and $R^5$ represents a $C_1 \sim C_8$ alkyl group, $C_2 \sim C_6$ alkenyl group, $C_3 \sim C_7$ cycloalkyl group which may be substituted by a $C_1 \sim C_3$ alkyl group, $C_1 \sim C_5$ haloalkyl group or phenyl group which may be substituted.

The present invention further provides an insecticidal and miticidal composition containing the pyrazolecarboxamide derivative represented by the formula (I) as the active ingredient.

The present invention still further provides a fungicidal composition for use in agriculture and horticulture containing the pyrazolecarboxamide derivative represented by the formula (I).

DETAILED DESCRIPTION OF THE INVENTION

In the formula (I), $R^1$ and $R^2$ independently represent a $C_1 \sim C_3$ alkyl group such as methyl group, ethyl group, n-propyl group and isopropyl group, and preferably methyl group or ethyl group.

$R^3$ represents a hydrogen atom or halogen atom such as fluorine, chlorine, bromine, etc., and preferably a hydrogen or chlorine atom.

$R^2$ and $R^3$ may combine each other to form a $C_3 \sim C_4$ alkylene group which may be substituted by a $C_1 \sim C_3$ alkyl group mentioned above and exemplified below.

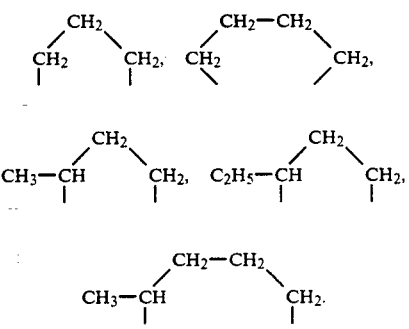

Preferred $C_3 \sim C_4$ alkylene group is a propylene group which may be substituted by a $C_1 \sim C_3$ alkyl group, and more preferred is

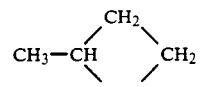

$R^4$ represents a $C_1 \sim C_6$ alkyl group, benzyl group which may be substituted or $-XR^5$, preferably a $C_1 \sim C_6$ alkyl group or $-XR^5$, more preferably $-XR^5$.

The $C_1 \sim C_6$ alkyl group may include methyl group, ethyl group, n-propyl group, isopropyl group, n-butyl group, isobutyl group, sec-butyl group, t-butyl group, n-pentyl group, isopentyl group, neopentyl group, t-pentyl group, 1-methylbutyl group, 2-methylbutyl group, 1-ethylpropyl group, 1,2-dimethylpropyl group, n-hexyl group, isohexyl group, neohexyl group, 1-methylpentyl group, 2-methylpentyl group, 3-methylpentyl group, 1-ethylbutyl group, 1,2,2-trimethylpropyl group, 1,1-dimethylbutyl group, 1-ethyl-1-methylpropyl group, etc. Of these alkyl groups, preferred is a $C_1 \sim C_4$ alkyl group, and more preferred are methyl group and isobutyl group.

The substituent for the benzyl group can be selected from halogen atoms such as fluorine, chlorine, bromine, etc.; $C_1 \sim C_4$ alkyl groups such as methyl group, ethyl group, n-propyl group, isopropyl group, n-butyl group, isobutyl group, sec-butyl group, t-butyl group, etc.; $C_1 \sim C_4$ haloalkyl groups such as fluoromethyl group, chloromethyl group, bromomethyl group, difluoromethyl group, dichloromethyl group, dibromomethyl group, trifluoromethyl group, trichloromethyl group, tribromomethyl group, 2,2,2-trifluoroethyl group, 2,2,2-trichloroethyl group, 2,2,2-tribromoethyl group, etc.; $C_3 \sim C_6$ cycloalkyl groups such as cyclopropyl group, cyclobutyl group, cyclopentyl group, cyclohexyl group, etc.; hydroxyl group; $C_1 \sim C_4$ alkoxy groups such as methoxy group, ethoxy group, n-propoxy group, isopropoxy group, n-butoxy group, isobutoxy group, sec-butoxy group, t-butoxy group, etc.; $C_1 \sim C_4$ haloalkoxy groups such as fluoromethoxy group, chloromethoxy group, bromomethoxy group, difluoromethoxy group, dichloromethoxy group, dibromomethoxy group, trifluoromethoxy group, trichloromethoxy group, tribromomethoxy group, 2,2,2-trifluoroethoxy group, 2,2,2-trichloroethoxy group, 2,2,2-tribromoethoxy group, etc.; mercapto group; $C_1 \sim C_4$ alkylthio groups such as methylthio group, ethylthio group, n-propylthio group, isopropylthio group, n-butylthio group, isobutylthio group, sec-butylthio group, t-butylthio group, etc.; $C_1 \sim C_4$ alkylsulfinyl groups such as methylsulfinyl group, ethylsulfinyl group, n-propylsulfinyl group, isopropylsulfinyl group, n-butylsulfinyl group, isobutylsulfinyl group, secbutylsulfinyl group, t-butylsulfinyl group, etc.; $C_1 \sim C_4$ alkylsulfonyl groups such as methylsulfonyl group, ethylsulfonyl group, n-propylsulfonyl group, isopropylsulfonyl group, n-butylsulfonyl group, isobutylsulfonyl group, sec-butylsulfonyl group, t-butylsulfonyl group, etc.; carboxyl group; $C_2 \sim C_5$ alkoxycarbonyl groups such as methoxycarbonyl group, ethoxycarbonyl group, n-propoxycarbonyl group, isopropoxycarbonyl group, n-butoxycarbonyl group, isobutoxycarbonyl, sec-butoxycarbonyl group, t-butoxycarbonyl group, etc.; cyano group; $C_1 \sim C_5$ acyl groups such as formyl group, acetyl group, propionyl group, n-butyryl group, isobutyryl group, n-valeryl group, isovaleryl group, pivaloyl group, etc.; hydroxymethyl group; $C_2 \sim C_5$ alkoxyalkyl groups such as methoxymethyl group, ethoxymethyl group, n-propoxymethyl group, isopropoxymethyl group, n-butoxymethyl group, isobutoxymethyl group, etc.; nitro group; amino group; $C_1 \sim C_4$ alkylamino groups such as methylamino group, ethylamino group, n-propylamino group, isopropylamino group, n-butylamino group, isobutylamino group, secbutylamino group, t-butylamino group, etc.; and $C_2 \sim C_6$ dialkylamino groups such as dimethylamino group, diethylamino group, di-n-propylamino group, diisopropylamino group, methylethylamino group, methyl-n-propylamino group, etc. Preferred substituents are $C_1 \sim C_4$ alkyl groups, and more preferred is methyl group.

In $-XR^5$, X represents an oxygen atom, sulfur atom, sulfinyl group or sulfonyl group, and preferably an oxygen atom or sulfur atom. $R^5$ represents a $C_1 \sim C_8$ alkyl group, $C_2 \sim C_6$ alkenyl group, $C_3 \sim C_7$ cycloalkyl group which may be substituted by a $C_1 \sim -C_3$ alkyl group, $C_1 \sim C_5$ haloalkyl group or phenyl group which may be substituted.

$C_1 \sim C_8$ alkyl group may include methyl group, ethyl group, n-propyl group, isopropyl group, n-butyl group, isobutyl group, sec-butyl group, t-butyl group, n-pentyl group, isopentyl group, neopentyl group, t-pentyl group, 1-methylbutyl group, 2-methylbutyl group, 1-ethylpropyl group, 1,2-dimethylpropyl group, n-hexyl group, isohexyl group, neohexyl group, 1-methylpentyl group, 2-methylpentyl group, 3-methylpentyl group, 1-ethylbutyl group, 1,2,2-trimethylpropyl group, 1,1-dimethylbutyl group, 1-ethyl-1-methylpropyl group, n-heptyl group, isoheptyl group, 1-methylhexyl group, 1-ethylpentyl group, 1-propylbutyl group, 1,3,3-trimethylbutyl group, 1,1-dimethylpentyl group, n-octyl group, 2-ethylhexyl group, 2-propylpentyl group, 1-methylheptyl group, 1-ethylhexyl group, 1,5-dimethylhexyl group, 1-ethyl-4-methylpentyl group, 1,1-dimethylhexyl group, 1,1,4-trimethylpentyl group, 3-ethyl-3-methylpentyl group, etc. Preferred is a $C_1 \sim C_6$ alkyl group and more preferred is a $C_3 \sim C_6$ alkyl group.

$C_2 \sim C_6$ alkenyl group may include vinyl group, 1-methylvinyl group, allyl group, 2-butenyl group, 3-butenyl group, 1-methylallyl group, 2-methylallyl group, 2-pentenyl group, 3-pentenyl group, 4-pentenyl group, 3-methyl-2-butenyl group, 2-methyl-3-butenyl group, 3-methyl-3-butenyl group, 1-methyl-2-butenyl group, 1-methyl-3-butenyl group, 2-hexenyl group, 3-hexenyl group, 4-hexenyl group, 5-hexenyl group, 4-methyl-3-pentenyl group, etc. Preferred alkenyl group is a $C_2 \sim C_4$ alkenyl group and more preferred is 3-butenyl group.

$C_3 \sim C_7$ cycloalkyl group which may be substituted by a $C_1 \sim C_3$ alkyl group may include cyclopropyl group, cyclobutyl group, cyclopentyl group, cyclohexyl group, cycloheptyl group, 2-methylcyclopropyl group, 1-methylcyclopentyl group, 2-methylcyclopentyl group, 3-methylcyclopentyl group, 1-methylcyclohexyl group, 2-methylcyclohexyl group, 3-methylcyclohexyl group, 4-methylcyclohexyl group, 4-ethylcyclohexyl group, etc. Preferred is a $C_3 \sim C_6$ cycloalkyl group which may be substituted by a $C_1 \sim C_3$ alkyl group, and more preferred is cyclopentyl group or a cyclohexyl group which may be substituted by a $C_1 \sim C_3$ alkyl group at the 4-position thereof.

$C_1 \sim C_5$ haloalkyl group may include fluoromethyl group, chloromethyl group, bromomethyl group, difluoromethyl group, dichloromethyl group, dibromomethyl group, trifluoromethyl group, trichloromethyl group, tribromomethyl group, 2-fluoroethyl group, 2-chloroethyl group, 2-bromoethyl group, 2,2,2-trifluoroethyl group, 2,2,2-trichloroethyl group, 2,2,2-tribromoethyl group, 3-fluoropropyl group, 3-chloropropyl group, 3-bromopropyl group, 3,3,3-trifluoropropyl group, 1-methyl-2,2,2-trifluoroethyl group, 1-(trifluoromethyl)-2,2,2-trifluoroethyl group, 2,2,3,3-tetrafluoropropyl group, 2,2,3,3,3-pentafluoropropyl group, 2,2-dichloro-3,3,3-trifluoropropyl group, 2,2,3,3,4,4,4-hepatafluorobutyl group, 2,2,3,3,4,4,5,5-octafluoropentyl group, etc. Preferred is a $C_1$–$C_3$ haloalkyl group, and more preferred is a $C_1 \sim C_3$ fluoroalkyl group.

The substituent for the phenyl group can be selected from halogen atoms such as fluorine, chlorine, bromine, etc.; $C_1 \sim C_4$ alkyl groups such as methyl group, ethyl group, n-propyl group, isopropyl group, n-butyl group, isobutyl group, sec-butyl group, t-butyl group, etc.; $C_1 \sim C_4$ haloalkyl groups such as fluoromethyl group, chloromethyl group, bromomethyl group, difluoromethyl group, dichloromethyl group, dibromomethyl group, trifluoromethyl group, trichloromethyl group, tribromomethyl group, 2,2,2-trifluoroethyl group, 2,2,2-trichloroethyl group, 2,2,2-tribromoethyl group, etc.; $C_3 \sim C_6$ cycloalkyl groups such as cyclopropyl group, cyclobutyl group, cyclopentyl group, cyclohexyl group, etc.; hydroxyl group; $C_1 \sim C_4$ alkoxy groups such as methoxy group, ethoxy group, n-propoxy group, isopropoxy group, n-butoxy group, isobutoxy group, sec-butoxy group, t-butoxy group, etc.; $C_1 \sim C_4$ haloalkoxy groups such as fluoromethoxy group, chloromethoxy group, bromomethoxy group, difluoromethoxy group, dichloromethoxy group, dibromomethoxy group, trifluoromethoxy group, trichloromethoxy group, tribromomethoxy group, 2,2,2-trifluoroethoxy group, 2,2,2-trichloroethoxy group, 2,2,2-tribromoethoxy group, etc.; mercapto group; $C_1 \sim C_4$ alkylthio groups such as methylthio group, ethylthio group, n-propylthio group, isopropylthio group, n-butylthio group, isobutylthio group, sec-butylthio group, t-butylthio group, etc.; $C_1 \sim C_4$ alkylsulfinyl groups such as methylsulfinyl group, ethylsulfinyl group, n-propylsulfinyl group, isopropylsulfinyl group, n-butylsulfinyl group, isobutylsulfinyl group, secbutylsulfinyl group, t-butylsulfinyl group, etc.; $C_1 \sim C_4$ alkylsulfonyl groups such as methylsulfonyl group, ethylsulfonyl group, n-propylsulfonyl group, isopropylsulfonyl group, n-butylsulfonyl group, isobutylsulfonyl group, sec-butylsulfonyl group, t-butylsulfonyl group, etc.; carboxyl group; $C_2 \sim C_5$ alkoxycarbonyl groups such as methoxycarbonyl group, ethoxycarbonyl group, n-propoxycarbonyl group, isopropoxycarbonyl group, n-butoxycarbonyl group, isobutoxycarbonyl, sec-butoxycarbonyl group, t-butoxycarbonyl group, etc.; cyano group; $C_1 \sim C_5$ acyl groups such as formyl group, acetyl group, propionyl group, n-butyryl group, isobutyryl group, n-valeryl group, isovaleryl group, pivaloyl group, etc.; hydroxymethyl group; $C_2 \sim C_5$ alkoxyalkyl groups such as methoxymethyl group, ethoxymethyl group, n-propoxymethyl group, isopropoxymethyl group, n-butoxymethyl group, isobutoxymethyl group, etc.; nitro group; amino group; $C_1 \sim C_4$ alkylamino groups such as methylamino group, ethylamino group, n-propylamino group, isopropylamino group, n-butylamino group, isobutylamino group, secbutylamino group, t-butylamino group, etc.; and $C_2 \sim C_6$ dialkylamino groups such as dimethylamino group, diethylamino group, di-n-propylamino group, diisopropylamino group, methylethylamino group, methyl-n-propylamino group, etc. Preferred substituent is a $C_1 \sim C_4$ alkyl group, $C_1 \sim C_4$ alkylthio group or $C_1 \sim C_4$ alkylsulfonyl group and more preferred is methyl group, methylthio group or methylsulfonyl group.

The present pyrazolecarboxamide derivative represented by the formula (I) can be produced in accordance with the following reaction schemes (1) or (2).

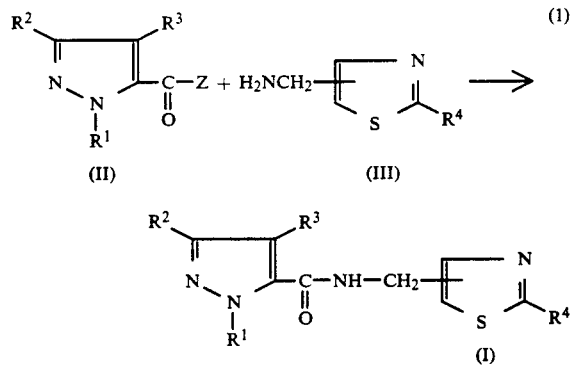

wherein $R^1$, $R^2$, $R^3$ and $R^4$ are the same as defined in the formula (I), and Z represents a chlorine, bromine, hydroxyl group, methoxy group, ethoxy group or propoxy group.

When Z represents chlorine atom or bromine atom, the compound of the formula (II) and the compound of the formula (III) are allowed to react in a solvent such as water; aromatic hydrocarbon such as benzene, toluene, xylene, etc.; halogenated hydrocarbon such as methylene chloride, chloroform, carbon tetrachloride, dichloroethane, etc.; ether such as diethyl ether, tetrahydrofuran, dioxane, etc.; ketone such as acetone, methyl ethyl ketone, etc.; ester such as methyl acetate, ethyl acetate, etc.; or polar solvent such as N,N-dimethylformamide, N-methylpyrrolidone, dimethylsulfoxide, sulfolane, acetonitrile, etc., preferably at $-20°$ to $60°$ C., more preferably at $0°$ to $20°$ C. in the presence of a base, thereby obtaining the compound of the formula (I). The base to be used may include an inorganic base such as sodium hydroxide, potassium hydroxide, sodium carbonate, potassium carbonate, sodium hydrogencarbonate and an organic base such as pyridine, triethylamine, etc.

When Z represents hydroxyl group, methoxy group, ethoxy group or propoxy group, the compound of the formula (II) and the compound the formula (III) are allowed to react without using a solvent or in a solvent having a high boiling point such as N,N-dimethylformamide, N-methylpyrrolidone, dimethylsulfoxide, sulfolane, etc. preferably at $150°$ to $250°$ C., or more preferably at $200°$ to $250°$ C.

Both the compounds as represented by the formulae (II) and (III) can be produced through the following known methods.

The compound of the formula (II) can be produced by, for example, the method described in Bull. Soc. Chim., France, 293(1966) or Ann. Chem., 536,97(1938).

The compound of the formula (III) can be produced by, for example, Gabriel synthesis from a 4- or 5-(halogenomethyl)thiazole derivative (IV) which is obtained by, for example, the method described in Japanese Patent Application Laid-Open (KOKAI) No. 61-183271 (1986).

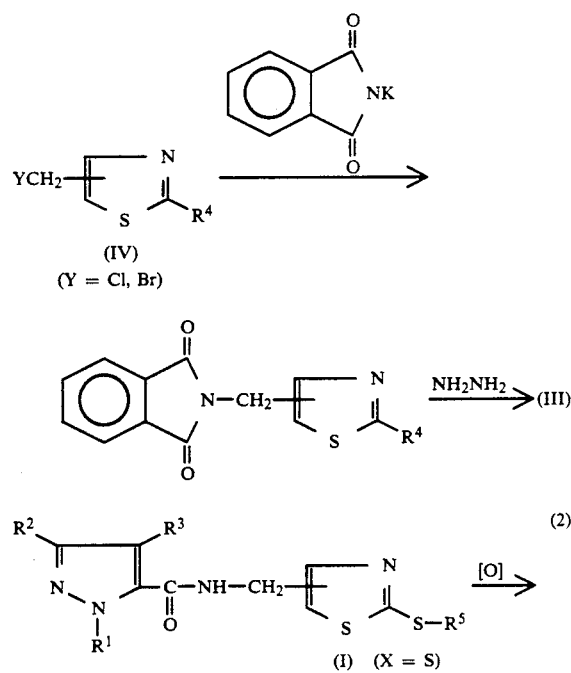

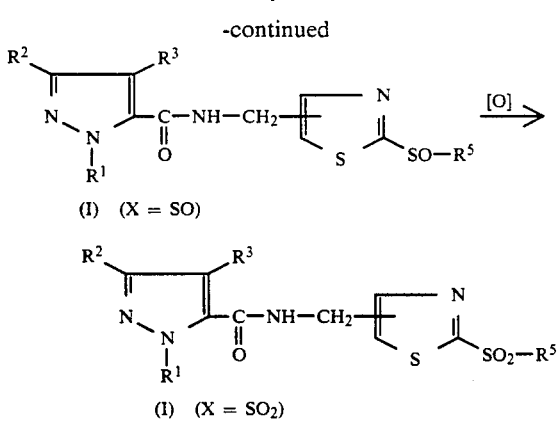

wherein R¹, R², and R³ and R⁵ are the same as defined in the formula (I).

In the formula (I), the compound where X represents sulfinyl group (referred to as "(I) (X=SO)"), or the compound where X represents sulfonyl group ((I) (X=SO₂)) can be produced by subjecting the compound where X represents sulfur atom ((I) (X=S)) to oxidation reaction by the action of an inorganic or organic oxidizing agent such as hydrogen peroxide, peracetic acid, methachloroperbenzoic acid, etc. in a solvent selected from water; acetic acid; aromatic hydrocarbon such as benzene, toluene, xylene, etc.; or halogenated hydrocarbon such as methylene chloride, chloroform, carbon tetrachloride, dichloroethane, etc., at −20° to 120° C., preferably at 0° to 80° C.

The compound of the formula (I) (X=SO) and the compound of the formula (I) (X=SO₂) can be obtained selectively by adjusting the amount of the oxidizing agent. It is preferred that the oxidizing agent is used by 0.9 to 1.5 equivalent to the compound of the formula (I) (X=S) for producing the compound of the formula (I) (X=SO) while it is used by 2 to 10 equivalent for producing the compound of the formula (I) (X=SO₂).

The compound of the formula (I) (X=SO) can be readily obtained according to the method (1) described above.

The pyrazolecarboxamide derivative of the present invention may be used alone as an insecticide, miticide or fungicide for agriculture and horticulture, but usually formulated into wettable powder, dust, emulsifiable concentrate, etc. by being mixed with an adjuvant as in ordinary agrochemicals, and used as such or after dilution. The adjuvant includes those used for common agrochemicals. They are, for example, solid carrier such as kaolin, bentonite, talc, diatomaceous earth, white carbon, starch, etc.; water; alcohol such as methanol, ethanol, propanol, butanol, ethylene glycol, etc.; ketone such as acetone, methyl ethyl ketone, cyclohexanone, etc.; ether such as diethyl ether, dioxane, cellosolve, etc.; aliphatic hydrocarbon such as. kerosine, lamp oil, etc.; aromatic hydrocarbon such as benzene, toluene, xylene, solvent naphtha, methylnaphthalene, etc.; halogenated hydrocarbon such as dichloroethane, trichlorobenzene, carbon tetrachloride, etc.; acid amides such as dimethylformamide, etc.; ester such as ethyl acetate, butyl acetate, glycerin ester of fatty acid, etc.; nitrile such as acetonitriles, etc.; and surfactant such as non-ionic surfactant including polyoxyethylene alkyl aryl ether, polyoxyethylene sorbitan monolaurate, etc.; cationic surfactant including alkyldimethylbenzylammonium chloride, alkylpyridinium chloride, etc.; anionic surfactant including alkylbenzenesulfonate, lignin-sulfonate, higher alcohol sulfate, etc.; and ampholytic surfactant including alkyldimethylbetaine, dodecilaminoethylglycine, etc. These solid carriers, solvents, and surfactants may be used alone or as a mixture of two or more according to individual needs. The content in a formulation of the compound of the present invention is not limited to a specific range, but preferably 1 to 90 weight % and more preferably 10 to 80 weight % for wettable powder; preferably 1 to 90 weight % and more preferably 10 to 50 weight % for dust; and preferably 1 to 90 weight % and more preferably 10 to 50 weight % for emulsifiable concentrate.

When the compound of the present invention is applied on plants as an insecticide, miticide, or fungicide for agriculture and horticulture, it is used as a solution or dispersion of a concentration of the active ingredient of preferably 1 to 1000 ppm, or more preferably 5 to 500 ppm. The application amount of the present compound depends on the insect and mite to be controlled, the disease to be controlled, the crop, the application method, etc., but preferably 10 to 3000 g per one hectare, more preferably 50 to 2000 g per one hectare.

In addition, the compound of the present invention can be used by being mixed with or in combination with other insecticides, miticides, fungicides for agriculture and horticulture, or plant growth controlling agents.

The compound of the formula (I) of the present invention has a remarkable controlling activity against insects belonging to Hemiotera, Lepidoptera, Coleoptera, Orthoptera and Diptera, and mites, but its use is not limited to them.

1. Hemiptera: Planthoppers such as *Sogatella frucifera, Nilaparvata lugens, Laodelphax striatellus*, etc.; leafhoppers such as *Nephotettix cincticeps, Cicadella viridis*, etc.; and Aphis such as *Myzus persicae*, etc.
2. Lepidoptera: *Plutella xylostella, Spodoptera litura, Chilo suppressalis, Cnaphalocrosis medinalis*, etc.
3. Coleoptera: *Callosobruchus chinensis*, etc.
4. Diptera: *Musca domestica, Aedes aegypti, Culex pipiens molestus*, etc.
5. Acarina: Tetranychidae such as *Tetranychus urticae, Tetranychus cinnabarinus, Panonychus citri*, etc.; Ixodidae such as *Boophilus* spp., *Ornithodoros* spp., etc., and Cheyletidae such as *Chelacaroosis moorei*

In addition, the compound of the present invention has a high control activity against the following pathogenic fungi of various plants, but its usage is not limited to them.

1. Blast causing fungi to rice plant.
2. Rust causing fungi to wheats.
3. Powdery mildew causing fungi to various crops.
4. Late blight or Phytophthora blight causing fungi to various crops.

The present invention will be explained in more detail referring to non-limitative synthetic examples, formulation examples and test examples.

EXAMPLE 1

Production of N-(2-n-propoxythiazol-5-5-ylmethyl)-4-chloro-3-ethyl-1-methylpyrazole-5-carboxamide (Compound No. 5 in Table 1)

0.52 g of 2-n-propoxythiazol-5-ylmethylamine and 0.36 g of triethylamine were dissolved in 15 ml of ethyl acetate and cooled on an ice bath, to which was added dropwise 0.62 g of 4-chloro-3-ethyl-1-methylprazole-5- carbonyl chloride with stirring. After the addition, the mixture was stirred for 2 hours at room temperature, to which was added water. The organic layer was washed with saturated aqueous sodium hydrogencarbonate, then with saturated aqueous sodium chloride, and dried over anhydrous magnesium sulfate. The solvent was distilled off under reduced pressure, and the residue was purified by silica-gel column chromatography (developing solvent: ethyl acetate/hexane=½) to obtain 0.79 g of the titled compound.

The NMR and IR spectra of this compound were as follows.

$^1$H-NMR (δ, CDCl$_3$): 7.04(1H, s), 4.63(2H, d), 4.33(2H, t), 4.13(3H, s), 2.62(2H, q), 1.88~1.74(2H, m), 1.23(3H, t), 1.01(3H, t)

IR(KBr)cm$^{-1}$: 3280, 1645, 1540, 1510, 1470, 1290, 1250, 1220, 1165, 970

Following similar procedures, the compounds Nos. 1 to 4, 6 to 19 and 24 to 31 as described in Tables 1 and 2 were produced.

EXAMPLE 2

Production of N-[2-(isopropylsulfinyl)thiazol-5-ylmethyl]-4-chloro-3-ethyl-1-methylpyrazole-5-carboxamide (compound No. 20 in Table 1)

0.65 g of N[2-(isopropylthio)thiazol-5-ylmethyl]-4-chloro-3-ethyl-1-methylpyrazole-5-carboxamide was dissolved in 20 ml of chloroform, to which was added little by little 0.40 g of metachloroperbenzoic acid, and the mixture was stirred at room temperature overnight. The resultant solution was washed with saturated aqueous sodium hydrogencarbonate, then with saturated aqueous sodium chloride, and dried over anhydrous magnesium sulfate. The solvent was distilled off under reduced pressure, and the residue was purified by silica-gel chromatography (developing solvent: ethyl acetate/hexane=2/1) to obtain 0.46 g of the titled compound.

The NMR and IR spectra of this compound were as follows.

$^1$H-NMR (δ, CDCl3): 7.85(1H, s), 4.92~4.78(2H, m), 4.13(3H, s), 3.21(1H, sept), 2.62(2H, q), 1.37(3H, d), 1.24(3H, d), 1.23(3H, t)

IR(KBr)cm$^{-1}$: 3380, 1650, 1530, 1505, 1285, 1270, 1050, 1030, 865, 555

Following similar procedures, the compound No. 21 as described in Table 1 was produced.

EXAMPLE 3

Production of N-[2-(isopropylsulfonyl)thiazol-5ylmethyl]-4-chloro-3-ethyl-1-methylpyrazole-5-carboxamide (compound No. 22 in Table 1)

0.65 g of N-[2-(isopropylthio)thiazol-5-ylmethyl]-4-chloro-3-ethyl-1-methylpyrazole-5-carboxamide was dissolved in 20 ml of chloroform, to which was added little by little 0.78 g of metachloroperbenzoic acid, and the mixture was stirred at room temperature overnight. The resultant solution was washed with saturated aqueous sodium hydrogencarbonate, then with saturated aqueous sodium chloride, and dried over anhydrous magnesium sulfate. The solvent was distilled off under reduced pressure, and the residue was purified by silica-gel chromatography (developing solvent: ethyl acetate/hexane=2/1) to obtain 0.54 g of the titled compound.

The NMR and IR spectra of this compound were as follows.

$^1$H-NMR (δ, CDCl3): 7.95(1H, s), 4.87(2H, d), 4.14(3H, s), 3.58(1H, sept), 2.63(2H, q), 1.41(6H, d), 1.24(3H, t)

IR(KBr)cm$^{-1}$: 3410, 1650, 1530, 1500, 1315, 1170, 1130, 875, 690

Following similar procedures, the compound No. 23 as described in Table 1 was produced.

TABLE 1

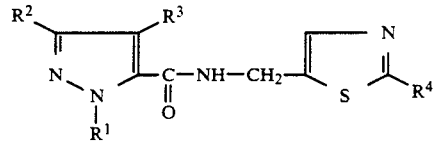

| Compound No. | R$^1$ | R$^2$ | R$^3$ | R$^4$ | Melting point |
|---|---|---|---|---|---|
| 1 | —CH$_3$ | —CH$_3$ | —Cl | —O—CH(CH$_3$)(CF$_3$) | 69~70° C. |
| 2 | " | —C$_2$H$_5$ | —H | " | ($n_D^{24.5}$1.5123) |
| 3 | " | " | —Cl | —CH$_3$ | 92~93° C. |
| 4 | " | " | " | -i-C$_4$H$_9$ | ($n_D^{21}$1.5521) |
| 5 | " | " | " | —O-n-C$_3$H$_7$ | 67.5~68° C. |
| 6 | " | " | " | —O-i-C$_3$H$_7$ | 65.5~66° C. |
| 7 | " | " | " | —O-n-C$_4$H$_9$ | 71.5~72° C. |
| 8 | " | " | " | —O-i-C$_4$H$_9$ | 80~80.5° C. |
| 9 | —CH$_3$ | —C$_2$H$_5$ | —Cl | —O-sec-C$_4$H$_9$ | 37~38° C. |
| 10 | " | " | " | —O-n-C$_5$H$_{11}$ | 67~68° C. |
| 11 | " | " | " | —O-i-C$_5$H$_{11}$ | 64~65° C. |
| 12 | " | " | " | —O-n-C$_6$H$_{13}$ | 67~67.5° C. |
| 13 | " | " | " | —O—CH$_2$CH$_2$CH=CH$_2$ | 65~66° C. |

TABLE 1-continued

[Structure: R² and R³ on pyrazole ring with N-R¹, connected via C(=O)-NH-CH₂- to a thiazole with R⁴]

| Compound No. | R¹ | R² | R³ | R⁴ | Melting point |
|---|---|---|---|---|---|
| 14 | " | " | " | —O-cyclopentyl | 69~69.5° C. |
| 15 | " | " | " | —O-(4-methylcyclohexyl) | Semi-solid |
| 16 | " | " | " | —O—CH₂CF₃ | 102~103° C. |
| 17 | " | " | " | —O—CH(CH₃)(CF₃) | 62.5~63.5° C. |
| 18 | " | " | " | —S-i-C₃H₇ | ($n_D^{23}$ 1.5818) |
| 19 | " | " | " | —S-i-C₄H₉ | 74.5~75° C. |
| 20 | " | " | " | —SO-i-C₃H₇ | 115.5~116° C. |
| 21 | " | " | " | —SO-i-C₄H₉ | 83~84° C. |
| 22 | " | " | " | —SO₂-i-C₃H₇ | 129.5~130° C. |
| 23 | —CH₃ | —C₂H₅ | —Cl | —SO₂-i-C₄H₉ | 99~100° C. |
| 24 | " | " | " | —CH₂—C₆H₄—CH₃ (p) | 98.5~99° C. |
| 25 | " | " | " | —O—C₆H₄—CH₃ (p) | 80.5~81.5° C. |
| 26 | " | " | " | —O—C₆H₄—SCH₃ (p) | 91.5~92.5° C. |
| 27 | " | " | " | —O—C₆H₄—SO₂CH₃ (p) | 144~145° C. |
| 28 | " | " | " | —S—C₆H₄—CH₃ (p) | 91~91.5° C. |
| 29 | " | CH₃-(cyclobutyl) | | —O—CH(CH₃)(CF₃) | Semi-solid |
| 30 | —C₂H₅ | —C₂H₅ | —Cl | " | 53~53.5° C. |

TABLE 2

| Compound No. | Structure | Melting point |
| --- | --- | --- |
| 31 | C₂H₅ group with pyrazole ring (N-N, CH₃), C(=O)-NH-CH₂- linked to thiazole with -O-CH(CH₃)(CF₃), Cl substituent | 62~63° C. |

The IR spectra of the Compounds Nos. 15 and 29 as described in Table 1 are listed in Table 3.

TABLE 3

| Compound No. | IR (KBr, cm$^{-1}$) |
| --- | --- |
| 15 | 3270, 1645, 1550, 1505, 1265, 1225, 1155, 1150, 975 |
| 29 | 3300, 1650, 1560, 1530, 1500, 1275, 1250, 1180, 1150, 1080, 1010, 660 |

Next, formulation examples will be described. It should to be noted that "part" and "%" in the following description means "weight part" and "weight %", respectively.

FORMULATION EXAMPLE 1

Wettable Powder

A wettable powder containing 20% of the active ingredient was prepared by uniformly mixing and pulverizing 20 parts of the compound No. 17 in Table 1, 20 parts of Carplex #80 (trademark, manufactured by Shionogi Seiyaku Co., Ltd.), 55 parts of Kunilite (trademark, manufactured by Kunimine Kogyo Co., Ltd.), and 5 parts of Sorpol 8070 (trademark, a higher alcohol sulfuric ester type surfactant manufactured by Toho Kagaku Co., Ltd.).

FORMULATION EXAMPLE 2

Dust

A dust containing 2% of the active ingredient was prepared by uniformly mixing and pulverizing 2 parts of the compound No. 17 in Table 1, 92.8 parts of clay (manufactured by Nippon Talc Co., Ltd.), 5 parts of white carbon, and 0.2 parts of isopropyl acid phosphate.

FORMULATION EXAMPLE 3

Emulsifiable Concentrate

An emulsifiable concentrate containing 20% of the active ingredient was prepared by dissolving 20 parts of the compound No. 17 in Table 1 into a mixed solvent of 32.5 parts of Kawakazol (trademark, manufactured by Kawasaki Kasei Co., Ltd.) and 32.5 parts of dimethylformamide, and adding thereto 15 parts of Sorpol 3005X (a polyoxyethylene type surfactant manufactured by Toho Kagaku Co., Ltd.).

FORMULATION EXAMPLE 4

Flowable Agent

A flowable agent containing 30% of the active ingredient was prepared by mixing and dispersing 30 parts of the compound No. 17 in Table 1, 8 parts of ethylene glycol, 5 parts of Sorpol AC3032 (trademark, manufactured by Toho Kagaku Co., Ltd.), and 0.1 part of xanthene gum into 56.9 parts of water, and then pulverizing the slurry mixture in wet process in a DYNO-MILL (manufactured by Shinmaru Enterprises Co., Ltd.).

Next, Test Examples of the present compounds will be described. The compound numbers listed in Tables 4 to 9 correspond to those in Table 1 and 2.

TEST EXAMPLE 1

Effect against larvae of Plutella xylostella

Each of the formulations prepared in accordance with the method of Formulation Example 1 was diluted with water containing 200 ppm of a spreader, Sorpol 3005X (trademark, manufactured by Toho Kagaku Co., Ltd.), to prepare a solution containing 500 ppm of the active ingredient.

Slices of cabbage leaves (5×5 cm) were immersed in the solution prepared above for one minute. They were air-dried after immersion and placed in a plastic cup (7 cm diameter), to which five larvae of third instar of *Plutella xylostella* were put and kept in a room maintained at a temperature of 25°±1° C. (two replicates).

Four days after the treatment, the numbers of dead and live larvae were counted to calculate the mortality from the following equation. The results are shown in Table 4.

$$\text{Mortality (\%)} = \frac{\text{Number of dead larvae}}{\text{Number of dead larvae + Number of live larvae}} \times 100$$

TABLE 4

| Compound No. | Mortality (%) |
| --- | --- |
| 1 | 100 |
| 2 | 100 |
| 3 | 60 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 80 |
| 21 | 100 |
| 22 | 70 |
| 24 | 100 |
| 25 | 100 |
| 26 | 100 |
| 27 | 100 |
| 28 | 100 |
| 29 | 100 |
| 30 | 100 |
| 31 | 80 |

TABLE 4-continued

| Compound No. | Mortality (%) |
|---|---|
| Untreated | 0 |

TEST EXAMPLE 2

Effect Against Larvae of *Nilaparvata lugens*

Each of the formulations prepared in accordance with the method of Formulation Example 1 was diluted with water containing 200 ppm of a spreader, Sorpol 3005X (trademark, manufactured by Toho Kagaku Co., Ltd.), to prepare a solution containing 500 ppm of the active ingredient.

Seedlings of rice plant and five larvae of *Nilaparvate lugens* were put into a glass cylinder with 2.5 cm diameter and 18 cm height. The top of the cylinder was covered with a mesh top cap. Then, 0.5 ml of the solution was scattered on the cylinder, and kept in a room maintained at a temperature 25°±1° C. (two replicates).

Five days after the treatment, the numbers of dead and live larvae in the cylinder were counted to calculate the mortality from the equation in Test Example 1. The results are shown in Table 5.

TABLE 5

| Compound No. | Mortality (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 90 |
| 25 | 100 |
| 26 | 100 |
| 27 | 90 |
| 28 | 100 |
| 29 | 100 |
| Untreated | 0 |

TEST EXAMPLE 3

Effect Against Adult of *Callosobruchus chinensis*

Each of the formulations prepared in accordance with the method of Formulation Example 1 was diluted with water containing 200 ppm of a spreader, Sorpol 3005X (trademark, manufactured by Toho Kagaku Co., Ltd.), to prepare a solution containing 500 ppm of the active ingredient.

Five adult of *Callosobruchus chinensis* and two grains of adzuki bean were put into a glass cylinder with 2.5 cm diameter and 18 cm height. The top of the cylinder was covered with a mesh top cap. Then, 0.5 ml of the solution was scattered on the cylinder, and kept in a room maintained at a temperature 25°±1° C. (two replicates).

Five days after the treatment, the numbers of dead and live adult in the cylinder were counted to calculate the mortality from the equation in Test Example 1. The results are shown in Table 6.

TABLE 6

| Compound No. | Mortality (%) |
|---|---|
| 1 | 80 |
| 2 | 100 |
| 4 | 90 |
| 5 | 100 |
| 6 | 100 |
| 7 | 100 |
| 8 | 100 |
| 9 | 70 |
| 10 | 100 |
| 11 | 100 |
| 12 | 60 |
| 13 | 100 |
| 14 | 80 |
| 15 | 100 |
| 16 | 100 |
| 17 | 100 |
| 18 | 100 |
| 19 | 100 |
| 20 | 100 |
| 24 | 90 |
| 25 | 100 |
| 26 | 100 |
| 28 | 100 |
| 29 | 100 |
| Untreated | 0 |

TEST EXAMPLE

Effect Against Adult and Eggs of *Tetranychus urticae*

Each of the formulations prepared in accordance with the method of Formulation Example 1 was diluted with water containing 200 ppm of a spreader, Sorpol 3005X (trademark, manufactured by Toho Kagaku Co., Ltd.), to prepare a solution containing 500 ppm of the active ingredient.

Ten female adult *Tetranychus urticae* were put on primary leaves of kidney bean and were allowed to oviposit on the leaves for 24 hours after putting. The leaves bearing the female adults and eggs were immersed in the solution prepared above for 5 sec, and thereafter, allowed to stand in a room maintained at a temperature of 25°±1° C. (two replicates).

Five days after the treatment, the numbers of live and dead adults were counted and the mortality was calculated from the equation in Test Example 1.

At the same time, the hatch of the eggs and the viability of the hatched larvae were observed. The ovicidal activity was evaluated by the following three ratings:

○: 0% viability
Δ: less than 20% viability
×: 20% or more viability

The results are shown in Table 7.

TABLE 7

| Compound No. | Mortality (%) | Ovicidal Activity |
|---|---|---|
| 1 | 100 | ○ |
| 2 | 100 | ○ |
| 3 | 100 | ○ |
| 4 | 100 | ○ |
| 5 | 100 | ○ |
| 6 | 100 | ○ |
| 7 | 100 | ○ |
| 8 | 100 | ○ |
| 9 | 100 | ○ |
| 10 | 100 | ○ |
| 11 | 100 | ○ |
| 12 | 100 | ○ |
| 13 | 100 | ○ |
| 14 | 100 | ○ |
| 15 | 100 | ○ |

TABLE 7-continued

| Compound No. | Mortality (%) | Ovicidal Activity |
| --- | --- | --- |
| 16 | 100 | ○ |
| 17 | 100 | ○ |
| 18 | 100 | ○ |
| 19 | 100 | ○ |
| 25 | 100 | ○ |
| 26 | 100 | ○ |
| 28 | 100 | ○ |
| 29 | 100 | ○ |
| 30 | 100 | ○ |
| Untreated | 0 | x |

TEST EXAMPLE 5

Controlling Effect on *Erysiphe graminis* of Wheat

Each of the formulations prepared in accordance with the method of Formulation Example 1 was diluted with water to prepare a solution containing 200 ppm of the active ingredient.

To wheat plants (species: Norin No. 61) nursed in pots of 6 cm diameter to 1 to 2-leaf stage, the solution prepared above was sprayed on the plants by foliage application at a rate of 10 ml per one pot. After the applied solution was air-dried, a suspension of spores obtained from wheat leaves infected with powdery mildew (*Erysiphe graminis*) was inoculated by spraying. The wheat plants thus treated were left to stand in a green house for 7 to 10 days. The ratio of disease area of each leaf was measured and the preventive value was calculated from the equation below.

$$\text{Preventive value (\%)} = \frac{\left(\begin{array}{c}\text{Average ratio of}\\\text{disease area in}\\\text{untreated pot}\end{array}\right) - \left(\begin{array}{c}\text{Average ratio of}\\\text{disease area in}\\\text{treated pot}\end{array}\right)}{\left(\begin{array}{c}\text{Average ratio of disease area}\\\text{in untreated pot}\end{array}\right)} \times 100$$

The results are shown in Table 8.

TABLE 8

| Compound No. | Preventive value (%) |
| --- | --- |
| 1 | 100 |
| 2 | 98 |
| 6 | 89 |
| 9 | 99 |
| 12 | 96 |
| 15 | 90 |
| 17 | 100 |
| 31 | 100 |
| Untreated | 0 |

TEST EXAMPLE 6

Controlling Effect on Puccinia recondita of Wheat

Each of the formulations prepared in accordance with the method of Formulation Example 1 was diluted with water to prepare a solution containing 200 ppm of the active ingredient.

To wheat plants (species: Norin No. 61) nursed in pots of 6 cm diameter to 1 to 2-leaf stage, the solution prepared above was sprayed on the plants by foliage application at a rate of 10 ml per one pot. After the applied solution was air-dried, a suspension of spores obtained by grinding wheat infected with brown rust (Puccinia recondita) was inoculated by spraying. The wheat plants thus treated were left to stand in a moist chamber at 22° C. for 15 hours and then in a green house for 7 days. The ratio of disease area of each leaf was measured and the preventive value was calculated from the equation in Text Example 5.

The results are shown in Table 9.

TABLE 9

| Compound No. | Preventive value (%) |
| --- | --- |
| 1 | 100 |
| 2 | 100 |
| 6 | 100 |
| 9 | 100 |
| 12 | 99 |
| 14 | 91 |
| 17 | 100 |
| 18 | 99 |
| 31 | 99 |
| Untreated | 0 |

What is claimed is:

1. A pyrazolecarboxamide derivative represented by the following formula (I):

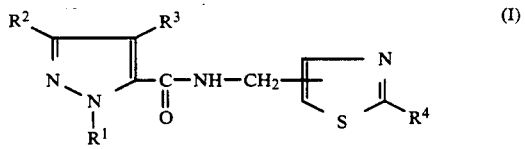

wherein $R^1$ represents a $C_1$–$C_3$ alkyl group, $R^2$ represents a $C_1$–$C_3$ alkyl group, $R^3$ represents a hydrogen atom or halogen atom, $R^2$ and $R^3$ may combine to form a $C_3$–$C_4$ alkylene group which may be substituted by a $C_1$–$C_3$ alkyl group, and $R^4$ represents a $C_1$–$C_6$ alkyl group, benzyl group which may be substituted by at least one substituent selected from the group consisting of halogen atom, $C_1$–$C_4$ alkyl group, $C_1$–$C_4$ haloalkyl group, $C_3$–$C_6$ cycloalkyl group, hydroxyl group, $C_1$–$C_4$ alkoxy group, $C_1$–$C_4$ haloalkyoxy group, mercapto group, $C_1$–$C_4$ alkylthio group, $C_1$–$C_4$ alkylsulfinyl group, $C_1$–$C_4$ alkylsulfonyl group, carboxyl group, $C_2$–$C_5$ alkoxycarbonyl group, cyano group, $C_1$–$C_5$ acyl group, hydroxymethyl group, $C_2$–$C_5$ alkoxyalkyl group, nitro group, amino group, $C_1$–$C_4$ alkylamino group, and $C_2$–$C_6$ dialkylamino group; or a group represented by —$XR^5$ wherein X represents an oxygen atom, sulfur atom, sulfinyl group or sulfonyl group, and $R^5$ represents a $C_1$–$C_8$ alkyl group, $C_2$–$C_6$ alkenyl group, $C_3$–$C_7$ cycloalkyl group which may be substituted by a $C_1$–$C_3$ alkyl group, $C_1$–$C_5$ haloalkyl group or phenyl group which may be substituted by at least one substituent selected from the group consisting of halogen atom, $C_1$–$C_4$ alkyl group, $C_1$–$C_4$ haloalkyl group, $C_3$–$C_6$ cycloalkyl group, hydroxyl group, $C_1$–$C_4$ alkoxy group, $C_1$–$C_4$ haloalkoxy group, $C_1$–$C_4$ alkylsulfonyl group, carboxyl group, $C_2$–$C_5$ alkoxycarbonyl group, cyano group, $C_1$–$C_5$ acyl group, hydroxymethyl group, $C_2$–$C_5$ alkoxyalkyl group, nitro group, amino group, $C_1$–$C_4$ alkylamino group, and $C_2$–$C_6$ dialkylamino group.

2. The pyrazolecarboxamide derivative according to claim 1, wherein $R^1$ represents a $C_1$–$C_2$ alkyl group, $R^2$ represents a $C_1$–$C_2$ alkyl group, $R^3$ represents a hydrogen atom or chlorine atom, $R^2$ and $R^3$ may combine to form propylene group which may be substituted by a $C_1$–$C_3$ alkyl group, and $R^4$ represents a $C_1$–$C_4$ alkyl group, benzyl group which may be substituted by a $C_1$–$C_4$ alkyl group or —$XR^5$ wherein X represents an oxygen atom, sulfur atom, sulfinyl group or sulfonyl group, and $R^5$ represents a $C_1$–$C_6$ alkyl group, $C_2$–$C_4$ alkenyl group, $C_3 \sim C_6$ cycloalkyl group which may be substituted by a $C_1 \sim C_3$ alkyl group, $C_1 \sim C_3$ haloalkyl group or phenyl group which may be substituted by at least one substituent selected from the group consisting of $C_1 \sim C_4$ alkyl group, $C_1 \sim C_4$ alkylthio group, and $C_1 \sim C_4$ alkylsulfonyl group.

3. An insecticidal and miticidal composition comprising as an active ingredient insecticidally and miticidally effective amount of the pyrazolecarboxamide derivative according to claim 1 and an insecticidally and miticidally acceptable adjuvant.

4. An insecticidal and miticidal composition comprising as an active ingredient insecticidally and miticidally effective amount of the pyrazolecarboxamide derivative according to claim 1 and an insecticidally and miticidally acceptable adjuvant.

5. An insecticidal and miticidal composition comprising as an active ingredient insecticidally and miticidally effective amount of the pyrazolecarboxamide derivative according to claim 2 and an insecticidally and miticidally acceptable adjuvant.

6. A fungicidal composition for use in agriculture and horticulture comprising as an active ingredient fungicidally effective amount of the pyrazolecarboxamide derivative according to claim 1 and a fungicidally acceptable adjuvant.

7. A fungicidal composition for use in agriculture and horticulture comprising as an active ingredient fungicidally effective amount of the pyrazolecarboxamide derivative according to claim 2 and a fungicidally acceptable adjuvant.

8. A fungicidal composition for use in agriculture and horticulture comprising as an active ingredient fungicidally effective amount of the pyrazolecarboxamide derivative according to claim 2 and a fungicidally acceptable adjuvant.

9. A fungicidal composition for use in agriculture and horticulture comprising as an active ingredient fungicidally effective amount of the pyrazolecarboxamide derivative represented by the formula (I):

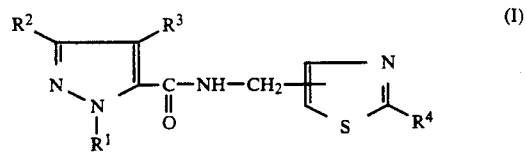

wherein $R^1$ represents a $C_1 \sim C_2$ alkyl group, $R^2$ represents a $C_1 \sim C_2$ alkyl group, $R^3$ represents a hydrogen atom or chlorine atom, and $R^4$ represents $-XR^5$ wherein X represents an oxygen atom or sulfur atom and $R^5$ represents a $C_1 \sim C_6$ alkyl group, $C_3 \sim C_6$ cycloalkyl group which may be substituted by a $C_1 \sim C_3$ alkyl group or $C_1 \sim C_3$ haloalkyl group, and a fungicidally acceptable adjuvant.

* * * * *